US008334686B2

(12) United States Patent
Sato (10) Patent No.: US 8,334,686 B2
(45) Date of Patent: Dec. 18, 2012

(54) VIBRATING HELICAL SPRING SENSORS AND METHODS TO OPERATE THE SAME

(75) Inventor: Shigeru Sato, Tokyo (JP)

(73) Assignee: Schlumberger Technology Corporation, Sugar Land, TX (US)

( * ) Notice: Subject to any disclaimer, the term of this patent is extended or adjusted under 35 U.S.C. 154(b) by 623 days.

(21) Appl. No.: 12/551,563

(22) Filed: Sep. 1, 2009

(65) Prior Publication Data

US 2011/0050233 A1 Mar. 3, 2011

(51) Int. Cl.
*G01P 3/48* (2006.01)
(52) U.S. Cl. ........................................... 324/166
(58) Field of Classification Search .................. None
See application file for complete search history.

(56) References Cited

U.S. PATENT DOCUMENTS

| | | | |
|---|---|---|---|
| 4,288,901 A | 9/1981 | Babcock | |
| 7,194,902 B1 | 3/2007 | Goodwin et al. | |
| 7,222,671 B2 | 5/2007 | Caudwell et al. | |
| 7,748,265 B2 * | 7/2010 | Reid et al. | 73/152.11 |
| 7,874,355 B2 * | 1/2011 | O'Keefe et al. | 166/173 |
| 2006/0137873 A1 * | 6/2006 | Caudwell et al. | 166/252.5 |
| 2007/0186684 A1 | 8/2007 | Pham | |
| 2008/0078581 A1 * | 4/2008 | Goodwin et al. | 175/50 |
| 2009/0078036 A1 * | 3/2009 | Terabayashi et al. | 73/152.55 |
| 2009/0078412 A1 * | 3/2009 | Kanayama et al. | 166/250.15 |
| 2009/0090172 A1 * | 4/2009 | Angelescu et al. | 73/54.14 |
| 2009/0120171 A1 | 5/2009 | Harrison et al. | |
| 2010/0206063 A1 * | 8/2010 | Fujisawa et al. | 73/152.24 |
| 2010/0241407 A1 * | 9/2010 | Hsu et al. | 703/2 |
| 2011/0252879 A1 * | 10/2011 | Madhavan et al. | 73/152.33 |

OTHER PUBLICATIONS

Sir G.G. Stokes, "On the Effect of the Internal Friction of Fluids on the Motion of Pendulums," Transactions of the Cambridge Philosophical Society, vol. IV, Dec. 9, 1950.

* cited by examiner

*Primary Examiner* — Jermele M Hollington
(74) *Attorney, Agent, or Firm* — Jianguang Du; Jody DeStefanis (57) ABSTRACT

Example vibrating helical spring sensors and methods to operate the same are disclosed. A disclosed example apparatus includes a housing, a helical spring held in tension, a flowline to expose the helical spring to a fluid, a magnet to expose the helical spring to a magnetic field, and a wire to electrically conduct an actuating current through the helical spring to displace the helical spring.

25 Claims, 8 Drawing Sheets

VIBRATING HELICAL SPRING SENSORS AND METHODS TO OPERATE THE SAME

FIELD OF THE DISCLOSURE

This patent relates generally to vibrating sensors and, more particularly, to vibrating helical spring sensors and methods to operate the same.

BACKGROUND

Wellbores are drilled to, for example, locate and produce hydrocarbons. During a drilling operation, it may be desirable to perform evaluations of the formations penetrated and/or encountered formation fluids. In some cases, a drilling tool is removed and a wireline tool is then deployed into the wellbore to test and/or sample the formation and/or fluids associated with the formation. In other cases, the drilling tool may be provided with devices to test and/or sample the surrounding formation and/or formation fluids without having to remove the drilling tool from the wellbore. These samples or tests may be used, for example, to characterize hydrocarbons.

Formation evaluation often requires fluid(s) from the formation to be drawn into the downhole tool for testing, evaluation and/or sampling. Various devices, such as probes, are extended from the downhole tool to establish fluid communication with the formation surrounding the wellbore and to draw fluid(s) into the downhole tool. Fluid(s) passing through and/or captured within the downhole tool may be tested and/or analyzed to determine various parameters and/or properties while the downhole tool is positioned in situ, that is, within a wellbore. Various properties of hydrocarbon reservoir fluids, such as viscosity, bubble point pressure, density and phase behavior of the fluid at reservoir condition may be used to evaluate potential reserves, determine flow in porous media and design completion, separation, treating, and metering systems, among others.

SUMMARY

Example vibrating helical spring sensors and methods to operate the same are disclosed. A disclosed example apparatus includes a housing, a helical spring held in tension, a flowline to expose the helical spring to a fluid, a magnet to expose the helical spring to a magnetic field, and a wire to electrically conduct an actuating current through the helical spring to displace the helical spring.

A disclosed example method includes positioning a helical spring within a fluid, passing a current through the helical spring to displace the helical spring within the fluid, measuring an electromotive force (emf) voltage induced across the helical spring by the displacement, and estimating a characterizing parameter of the fluid from the measured emf voltage.

Another disclosed example apparatus includes a helical spring held under tension in a fluid passageway, an actuating device to induce a displacement of the helical spring while a fluid is present in the fluid passageway, and an interpretation module to estimate a parameter of the fluid based the induced displacement of the helical spring.

Certain examples are shown in the above-identified figures and described in detail below. In describing these examples, like or identical reference numbers may be used to identify common or similar elements. The figures are not necessarily to scale and certain features and certain views of the figures may be shown exaggerated in scale or in schematic for clarity and/or conciseness. Moreover, while certain preferred embodiments are disclosed herein, other embodiments may be utilized and structural changes may be made without departing from the scope of the invention.

DETAILED DESCRIPTION

In a vibrating wire sensor, a wire is held under tension within a fluid moving through a fluid passageway. The wire comprises an electrically conductive material and is displaced from an initial position by a current passing through the wire in the presence of a magnetic field. The motion of the vibrating wire is determined by measuring the electromotive force (emf), which is a voltage that develops and/or which is induced across the wire as a result of the temporal change of the magnetic flux passing through a loop partially defined by the location of the vibrating wire. As the displacement of the wire depends on one or more characteristics of the fluid, in addition to the current and the magnetic field, an interpretation unit within a downhole tool or at a surface location can determine and/or estimate one or more parameters of the fluid based on the measured emf. Example fluid parameters that may be estimated include, but are not limited to, fluid viscosity $\eta$ and fluid density $\rho_f$. The vibrations and/or displacements of the wire can be excited and detected using any number and/or type(s) of method(s) and/or technique(s). In some examples, the current passed through the wire is at different frequencies and the emf is measured for each frequency to identify a resonant frequency of the wire. Such a measurement technique is known as a steady state approach. Additionally or alternatively, the vibrating wire may be driven temporarily from its stationary and equilibrium initial position, and the attenuation of the motion measured as function of time. For the purposes of clarity, this measurement technique will be referred to herein as a transient approach.

The example vibrating helical spring sensors disclosed herein provide certain advantages over existing vibrating wire sensors. Traditionally, straight segments of wire are used to implement vibrating wire sensors. However, by using wired formed into a helical spring rather than a straight wire segment, a number of advantages can be realized. First, the total wire length in contact with the fluid is increased enabling a more compact sensor design. Second, a larger elastic displacement can be induced in a helical spring than can be induced in a straight vibrating wire, thereby increasing the signal-to-noise ratio under linear vibration conditions.

While example helical spring sensors are described herein with reference to example downhole tools, it should be understood that the example helical spring sensors described herein can be used to perform fluid analysis at other locations. For example, the example helical spring sensors may be used to perform fluid analysis at a wellsite, in a transportable lab and/or at a fixed-location lab.

Figure 1:
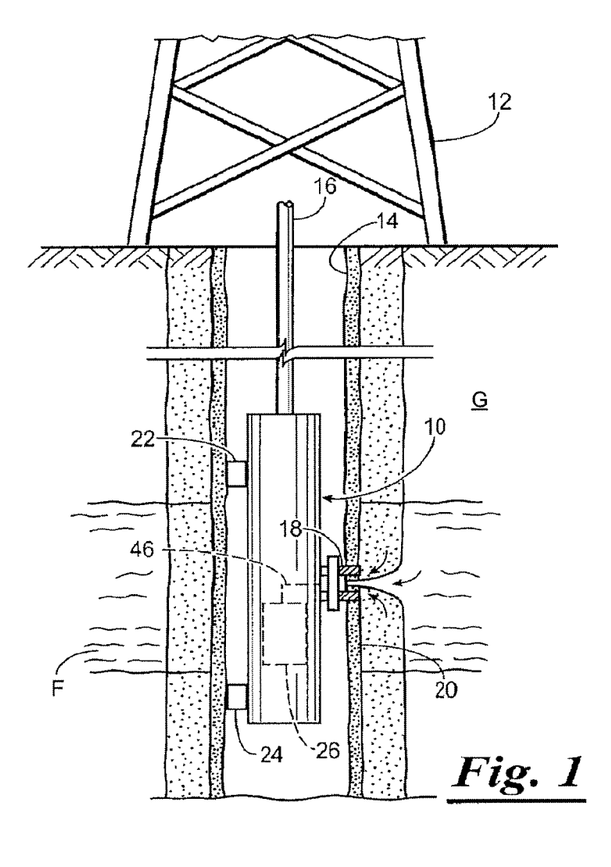
FIG. 1 is a schematic, partial cross-sectional view of a downhole wireline tool suspended from a rig and having an internal fluid analysis assembly.

FIG. 1 shows a schematic, partial cross-sectional view of an example downhole tool 10. The example downhole tool 10 of FIG. 1 is suspended from a rig 12 in a wellbore 14 formed in a geologic formation G. The example downhole tool 10 can implement any type of downhole tool capable of performing formation evaluation, such as x-ray fluorescence, fluid analysis, fluid sampling, well logging, etc. The example downhole tool 10 of FIG. 1 is a wireline tool deployed from the rig 12 into the wellbore 14 via a wireline cable 16 and positioned adjacent to a particular geologic formation F.

To seal the example downhole tool 10 of FIG. 1 to a wall 20 of the wellbore 14 (hereinafter referred to as a "wall 20" or "wellbore wall 20"), the example downhole tool 10 includes a probe 18. The example probe 18 of FIG. 1 forms a seal against the wall 20 and draws fluid(s) from the formation F into the downhole tool 10 as depicted by the arrows. Backup pistons 22 and 24 assist in pushing the example probe 18 of the downhole tool 10 against the wellbore wall 20.

To perform fluid analysis, the example downhole tool 10 of FIG. 1 includes a fluid analysis assembly 26 having a vibrating helical spring sensor 315 (FIG. 3) constructed in accordance with the teachings of this disclosure. The example fluid analysis assembly 26 receives formation fluid(s) from the probe 18 via an evaluation flowline 46. An example manner of implementing the example fluid analysis assembly 26 of FIG. 1 is described below in connection with FIGS. 3-7.

Figure 2:
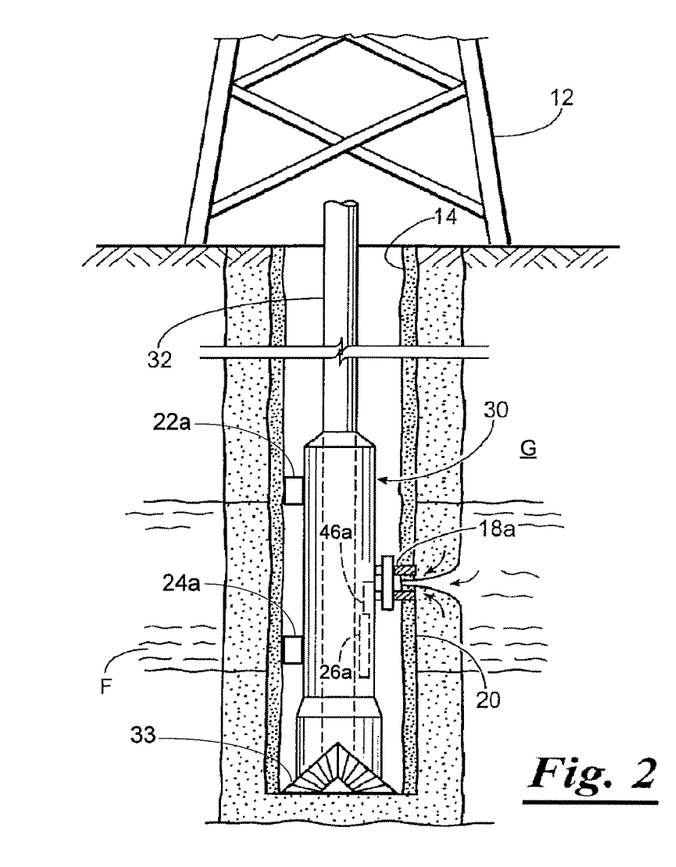
FIG. 2 is a schematic, partial cross-sectional view of a downhole drilling tool suspended from a rig and having an internal fluid analysis assembly.

FIG. 2 shows a schematic, partial cross-sectional view of another example of a downhole tool 30. The example downhole tool 30 of FIG. 2 can be conveyed among one or more of (or itself may be) a measurement-while-drilling (MWD) tool, a logging-while-drilling (LWD) tool, or other type of downhole tool that are known to those skilled in the art. The example downhole tool 30 is attached to a drillstring 32 and a drill bit 33 driven by the rig 12 and/or a mud motor (not shown) driven by mud flow to form the wellbore 14 in the geologic formation G.

To seal the example downhole tool 30 of FIG. 2 to the wall 20 of the wellbore 14, the downhole tool 30 includes a probe 18a. The example probe 18a of FIG. 2 forms a seal against the wall 20 to draw fluid(s) from the formation F into the downhole tool 30 as depicted by the arrows. Backup pistons 22a and 24a assist in pushing the example probe 18a of the downhole tool 30 against the wellbore wall 20. Drilling is stopped before the probe 18a is brought in contact with the wall 20.

Figure 3:
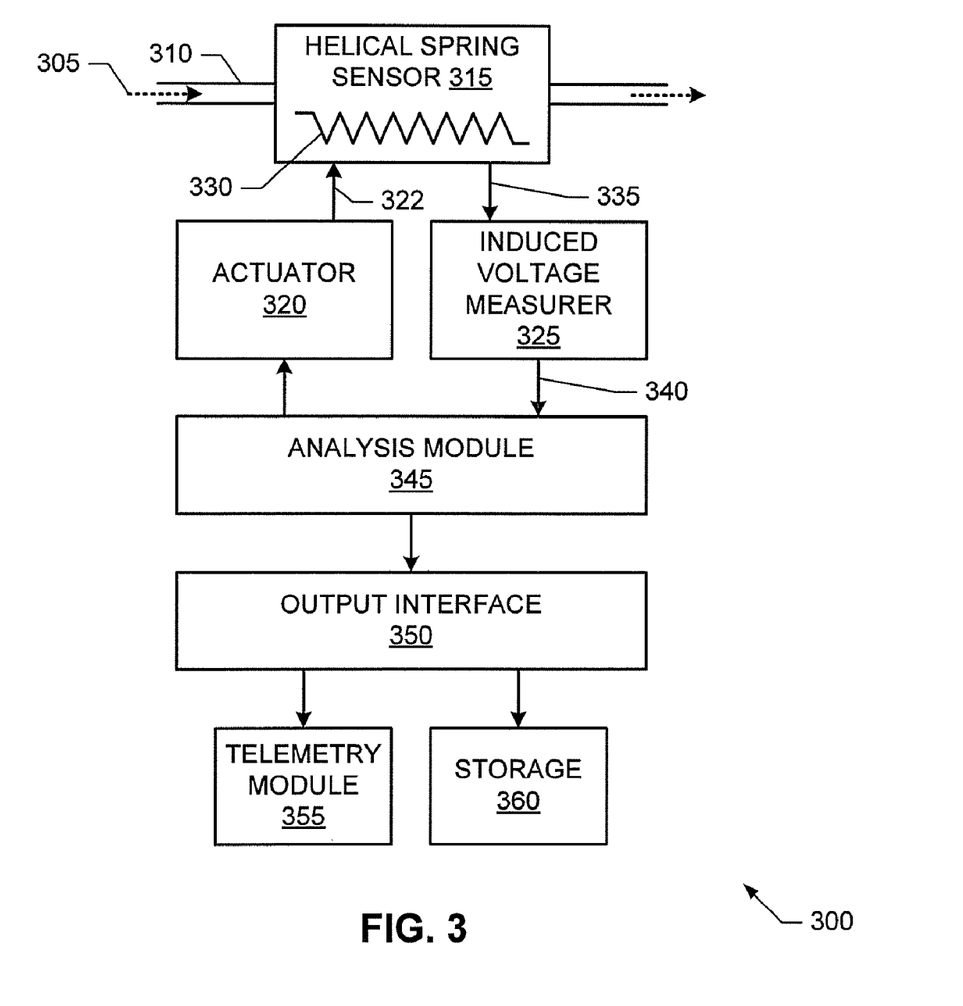
FIG. 3 illustrates an example manner of implementing the example fluid analysis assemblies of FIGS. 1 and 2.

To perform fluid analysis, the example downhole tool 30 of FIG. 2 includes a fluid analysis assembly 26a having the example vibrating helical spring sensor 315 (FIG. 3). The example fluid analysis assembly 26a receives formation fluid(s) from the probe 18a via an evaluation flowline 46a. An example manner of implementing the example fluid analysis assembly 26a of FIG. 2 is described below in connection with FIGS. 3-7.

FIG. 3 illustrates an example manner of implementing the example fluid analysis assemblies 26 and 26a of FIGS. 1 and 2. While either of the example fluid analysis assemblies 26 and 26a may be implemented by the example of FIG. 3, for ease of discussion, the illustrated example of FIG. 3 will be referred to as fluid analysis assembly 300.

Figure 4:
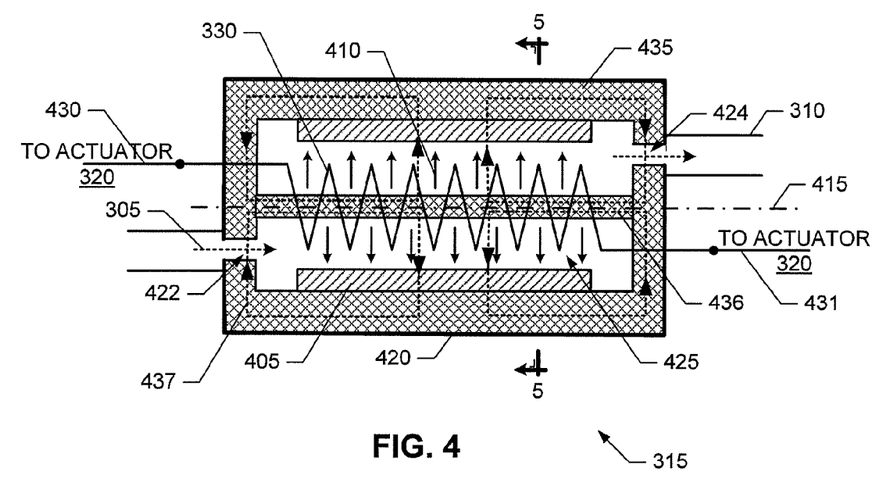
FIGS. 4-7 are cross-sectional views illustrating example manners of implementing the example vibrating helical spring sensor of FIG. 3.
Figure 5:
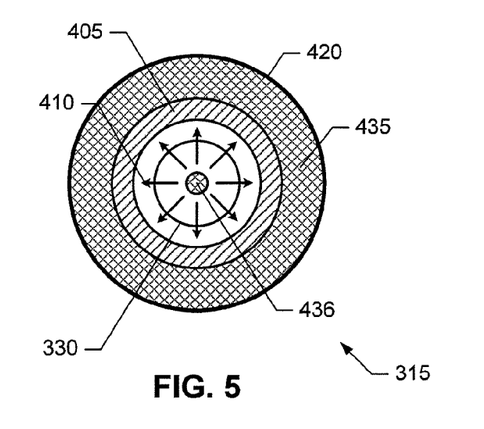

To take characterizing measurements of a fluid 305 flowing in and/or through a fluid passageway, channel and/or flowline 310, the example fluid analysis assembly 300 of FIG. 3 includes a helical spring sensor 315, an actuator 320 and an induced voltage measurer 325. The example helical spring sensor 315 of FIG. 3 comprises a helical spring 330 formed from an electrically conductive wire. The example helical spring 330 is held in tension within the helical spring sensor 315 within the fluid 305. Example manners of implementing the example helical spring sensor 315 of FIG. 3 are described below in connection with FIGS. 4-7. As illustrated in FIGS. 4 and 5, the example helical spring sensor 315 includes a permanent magnet 405 to form a magnetic field 410 that radiates radially from a longitudinal axis 415 of the helical spring 330.

The example actuator 320 of FIG. 3 includes any number and/or type(s) of current source(s) to actuate, activate and/or induce displacement(s) of the helical spring 330 by passing a current 322 through the helical spring 330. The current 322 passed through the helical spring 330 by the actuator 320 may be any type of current including, but not limited to, a steady-state current, an alternating current and/or a transient current. The displacement of the helical spring 330 depends on the type of current 322, the magnetic field 410, and one or more characteristics of the fluid 305. For example, a vibration of the helical spring 330 may be induced by passing an alternating current 322 through the helical spring 330. Additionally or alternatively, a transient oscillation of the helical spring 330 may be induced by passing a short burst of an alternating current 322 or a DC current 322 through the helical spring 330.

The example induced voltage measurer 325 of FIG. 3 measures an emf voltage 335 induced and/or developed across the helical spring 330 in response to the displacement of the helical spring 330. As the helical spring 330 moves over time in response to the current 322 and the magnetic field 410, the measured emf voltage 335 varies as a function of time. In the illustrated example of FIG. 3, the induced voltage measurer 325 outputs digital samples 340 representative of the induced emf voltage(s) 335. For ease of discussion, the digital samples 340 will be referred to as emf voltages 340.

Figure 8:
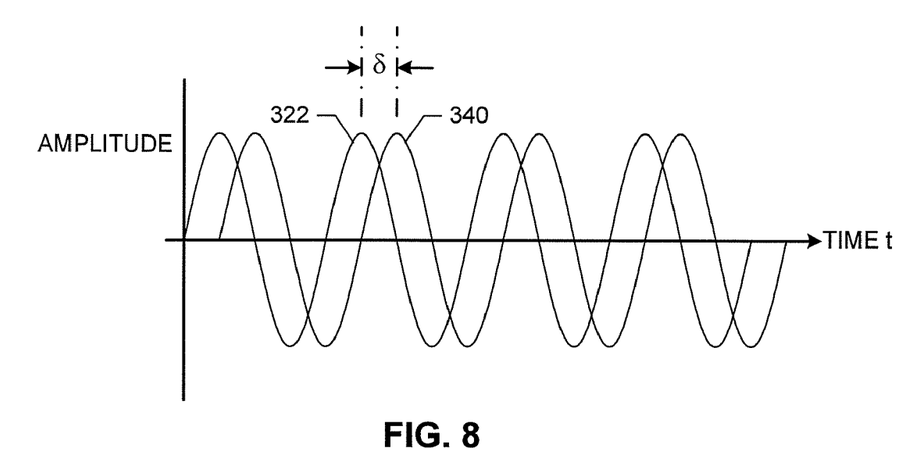
FIGS. 8-10 are graphs illustrating example methods of determining a drag force from measured induced displacements of the example vibrating helical spring sensors of FIGS. 3-7.
Figure 9:
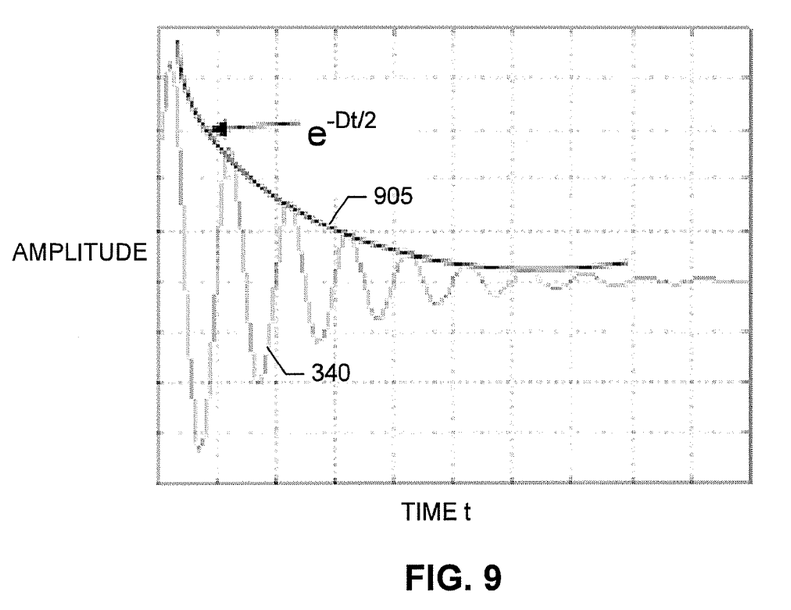
Figure 10:
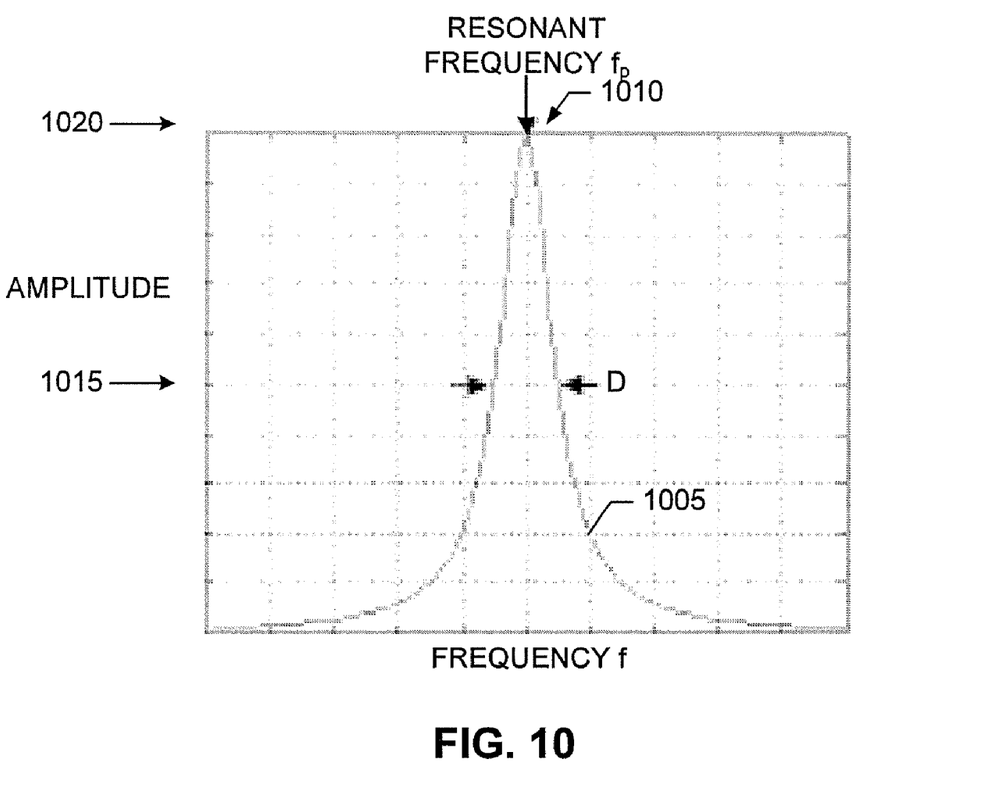

To determine, compute and/or otherwise estimate one or more parameters of the fluid 305, the example fluid analysis assembly 300 of FIG. 3 includes any number and/or type(s) of analysis modules, one of which is designated at reference numeral 345. Based on the measured emf voltages 340, the example analysis module 345 of FIG. 3 determines the dragging force D of the fluid 305. Example methods to determine the dragging force D from the measured emf voltages 340 are shown in FIGS. 8-10. In the illustrated example of FIG. 8, the helical spring 330 is vibrated at its resonant frequency $f_p$, and the example analysis module 345 measures and/or determines the phase difference $\delta$ between the current 322 and the measured emf voltages 340. The dragging force D is related to the phase difference $\delta$ as shown by the following mathematical expression $$\tan(\delta) = \frac{D\gamma}{\gamma^2 - \omega_0^2}, \qquad \text{EQN (1)}$$

where $\gamma$ is the external force frequency and $\omega_0$ is the resonant frequency $f_p$ in radians/sec (i.e., $\omega_0 = 2\pi f_p$).

In the illustrated example of FIG. 9, the dragging force D is determined from the damping factor of the helical spring 330. When excitation of the helical spring 330 is ceased, the measured emf voltages 340 decays over time t along a curve 905 defined by the mathematical expression $e^{-Dt/2}$. Accordingly, the example analysis module 345 can determine the dragging force D by fitting an exponential curve to the measured emf voltages 340 and solving for the dragging force D.

In the illustrated example of FIG. 10, the dragging force D is determined by measuring the amplitude 1005 of the emf voltages 340 for different alternating frequencies f of the current 322. A peak 1010 of the measured amplitudes 1005 corresponds to the resonant frequency $f_p$ of the helical spring 330. As shown in FIG. 10, the analysis module 345 can determine the dragging force D by determining the half-width of the measured amplitude curve 1005. That is, the dragging force D is the width of the measured amplitudes curve 1005 taken at an amplitude 1015 that is one-half the amplitude 1020 at the resonant frequency $f_p$.

Returning to FIG. 3, one or more additional properties of the fluid 305 can be determined from the dragging force D and one or more parameters of the helical spring 330. For example, the analysis module 345 can calculate, estimate and/or solve for the viscosity η of the fluid 305 using the well-known Stokes theory, which was described by Sir G. G. Stokes in a paper entitled "On the Effect of the Internal Friction of Fluids on the Motion of Pendulums," published in the Transactions of the Cambridge Philosophical Society, Vol. IV, Dec. 9, 1950, which is hereby incorporated by reference in its entirety. For example, the viscosity η can be solved using the following mathematical expression $$D = \pi i \gamma^2 \left(1 + \frac{4K_1(\sqrt{i}\lambda)}{(\sqrt{i}\lambda)K_0(\sqrt{i}\lambda)}\right), \quad \text{EQN (2)}$$

where $$\lambda = \frac{\omega \rho r^2}{\eta}, \quad \text{EQN (3)}$$

$K_0$ and $K_1$ are the modified Bessel functions of the first and second kind, respectively, λ is related to the Reynolds number that characterizes the flow around a cylindrical wire of radius r at the resonant frequency ω, and ρ is the density of the helical spring 330.

The example analysis module 345 can determine the density $\rho_f$ of the fluid 305 by, for example, solving the following mathematical expression $$\omega = \frac{r}{4nR^2}\sqrt{\frac{2G}{\rho_f}}, \quad \text{EQN (4)}$$

where r is the radius of the wire used to form the helical spring 330, R is the radius the helical spring 330, n is the number of turns in the helical spring 330, and G is the shear modulus of the wire used to form the helical spring 330.

Additional and/or alternative example methods that the analysis module 345 of FIG. 3 may implement to determine properties of the fluid 305 from measurements collected using the example helical spring sensor 315 are described in U.S. Pat. No. 7,194,902, entitled "Apparatus and Method for Formation Evaluation;" U.S. Pat. No. 7,222,671, entitled "Apparatus and Method for Formation Evaluation;" and U.S. Publication 2009/0120171, entitled "Vibrating Wire Viscosity Sensor," and filed Nov. 8, 2007, all of which are under obligation of assignment to the assignee of the present patent, and all of which are incorporated herein by reference in their entireties.

To output the computed parameters of the fluid 305, the example fluid analysis assembly 300 of FIG. 3 includes any number and/or type(s) of output interface(s), one of which is designated at reference numeral 350. The example output interface 350 of FIG. 3 sends some or all of the computed parameters and/or the measured emf voltages 340 to a surface location via any type of telemetry and/or data transmission module 355, and/or may store the computed model parameters and/or the measured emf voltages 340 in any number and/or type(s) of memory(-ies), memory device(s), storage and/or storage device(s) 360.

While an example manner of implementing the example fluid analysis assemblies 26 and 26a of FIGS. 1 and 2 has been illustrated in FIG. 3, one or more of the elements, sensors, circuits, modules, processes and/or devices illustrated in FIG. 3 may be combined, divided, re-arranged, omitted, eliminated and/or implemented in any other way. For example, the analysis module 345 may be implemented a surface location with the emf voltages 340 sent to the analysis module 345 at the surface location via the telemetry module 355, and/or the emf voltages 340 may be transferred from the storage 360 to the analysis module 345 at the surface location when the fluid analysis assembly 300 is withdrawn and/or retrieved from the wellbore 20. Further, the example helical spring sensor 315, the example actuator 320, the example induced voltage measurer 325, the example analysis module 345, the example output interface 350, the example telemetry module 355, the example storage 360 and/or, more generally, the example fluid analysis assembly 300 of FIG. 3 may be implemented by hardware, software, firmware and/or any combination of hardware, software and/or firmware. Thus, for example, any or all of the example helical spring sensor 315, the example actuator 320, the example induced voltage measurer 325, the example analysis module 345, the example output interface 350, the example telemetry module 355, the example storage 360 and/or, more generally, the example fluid analysis assembly 300 may be implemented by one or more circuit(s), programmable processor(s), application specific integrated circuit(s) (ASIC(s)), programmable logic device(s) (PLD(s)), field-programmable logic device(s) (FPLD(s)), field-programmable gate array(s) (FPGA(s)), etc. Further still, the fluid analysis assembly 300 may include elements, sensors, circuits, modules, processes and/or devices instead of, or in addition to, those illustrated in FIG. 3 and/or may include more than one of any or all of the illustrated elements, sensors, circuits, modules, processes and/or devices.

FIG. 4 is a side cross-sectional view of an example manner of implementing the example vibrating helical spring sensor 315 of FIG. 3. FIG. 5 is an end cross-sectional view of the example vibrating helical spring sensor 315 of FIG. 4 taken along line 5-5. The example helical spring sensor 315 of FIGS. 3 and 4 is contained and/or implemented within a cylindrically-shaped housing 420. The example housing 420 of FIG. 4 has the same longitudinal axis 415 as the helical spring 330. An inlet 422 and an outlet 424 are defined in the housing 420 to allow the example fluid 305 to pass through the helical spring sensor 315. As shown in FIG. 4, the example inlet 422, the example housing 420 and the example outlet 424 form a fluid channel and/or passageway 425 within the helical spring sensor 315 through which the fluid 310 can flow.

As shown in FIGS. 4 and 5, the example helical spring 330 comprises an electrically conductive wire that is coiled and/or spiraled about the longitudinal axis 415 to form the helical spring 330. In some examples, the helical spring 330 and the housing 420 are formed from Tungsten (W) and/or a Tungsten alloy having a Young's modulus of 470 kN/m$^2$. Preferably the housing 420 and the helical spring 330 have a substantially similar and/or substantially equal thermal expansion coefficient to substantially eliminate a change in the tension of the helical spring 330 due to an ambient and/or fluid temperature change. Ends of the example helical spring 330 are firmly attached to posts, clamps and/or any other means to which an end of a wire may be securely affixed, which are not shown for clarity of illustration. The helical spring 330 is held in tension within the fluid passageway 425 and, thus, is exposed to a flow of the fluid 305. The example actuator 320 of FIG. 4 is electrically coupled to the ends of the helical spring 330 via respective wires 430 and 431.

To form the magnetic field 410, the example helical spring sensor 315 includes the cylindrically-shaped permanent magnet 405. As shown in the illustrations of FIGS. 4 and 5, the example magnetic field 410 radiates radially from the longitudinal axis 415 along the length of the helical spring 330. In some examples, the permanent magnet 405 comprises Samarian-cobalt (SmCo) having a Curie temperature of 780-800° C.

To prevent the housing 420 or any magnetic field outside the housing 420 from interfering with the magnetic field 410, the example helical spring sensor 315 of FIGS. 4 and 5 contains high relative magnetic permeable materials 435 and 436. As shown in FIGS. 4 and 5, the material 435 is cylindrically shaped and positioned around the permanent magnet 405, and the material 436 is cylindrically shaped and positioned within the helical spring 330. In some examples, the magnetic materials 435 and 436 comprise a permalloy having a relative magnetic permeability of 8000 $\mu/\mu_0$. Because the example materials 435 and 436 are in contact with each other in the example of FIG. 4, they collectively form closed magnetic loops of magnetic flux within the vibrating spring sensor 315, one of which is designated at reference numeral 437.

In some example operations of the example vibrating spring sensor 315 of FIGS. 4 and 5, the actuator 320 passes an alternating current 322 through the helical spring 330 via the wires 430 and 431. That is, the current 322 flows back and forth (i.e., left and right in the example of FIG. 4) in the helical spring 330 in an alternating fashion. As shown in FIG. 10, the helical spring 330 vibrates with different amplitudes for different frequencies f of the alternating current 332, with the largest amplitude occurring at the resonant frequency $f_p$. In additional or alternative examples, the alternating current 322 is passed through the helical spring 330 to initiate a vibration of the helical spring 330 and then the alternating current 322 is stopped. As shown in FIG. 9, the amplitude of the vibrations will decay overtime when the alternating current 322 is stopped, with the rate of decay dependent on the dragging force D.

Figure 6:
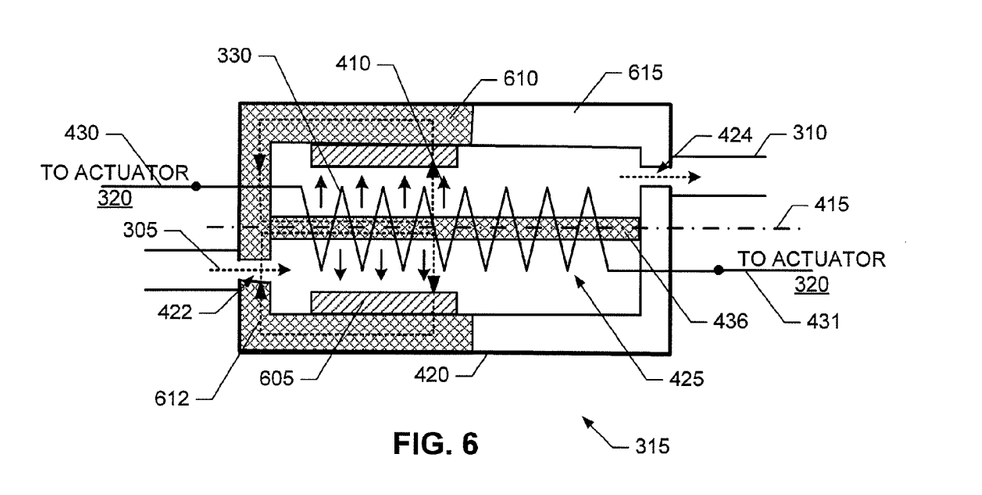

FIG. 6 is a side cross-sectional view of an alternative implementation of the example vibrating helical spring sensor 315 of FIG. 3. Because elements of the example vibrating helical spring sensor 315 of FIG. 6 are identical to those discussed above in connection with FIGS. 4 and 5, the description of identical elements is not repeated here. Instead, identical elements are illustrated with identical reference numerals in FIGS. 4, 5 and 6, and the interested reader is referred back to the descriptions presented above in connection with FIGS. 4 and 5 for a complete description of those like numbered elements.

In the illustrated example of FIG. 6, high relative magnetic permeable material 605 does not extend the length of the helical coil 330. Likewise, high relative magnetic permeable material 610 only encompasses a portion of the length of the helical coil 330. A portion 615 of the example sensor 315 of FIG. 6 comprises a non high magnetic permeable material. Because the example materials 605 and 610 are in contact with each other in the example of FIG. 6, they collectively form closed magnetic loops of magnetic flux, one of which is designated at reference numeral 612, within the vibrating spring sensor 315 around the portion of the helical coil 330 encompassed by the materials 605 and 610. Accordingly, when an alternating current 322 (FIG. 3) is passed through the helical coil 330 via the wires 430 and 431, only the portion of the helical spring 330 surrounded by the permanent magnet 605 vibrates, with the remaining portion of the helical spring 330 expanding and shrinking along the longitudinal axis 415

Figure 7:
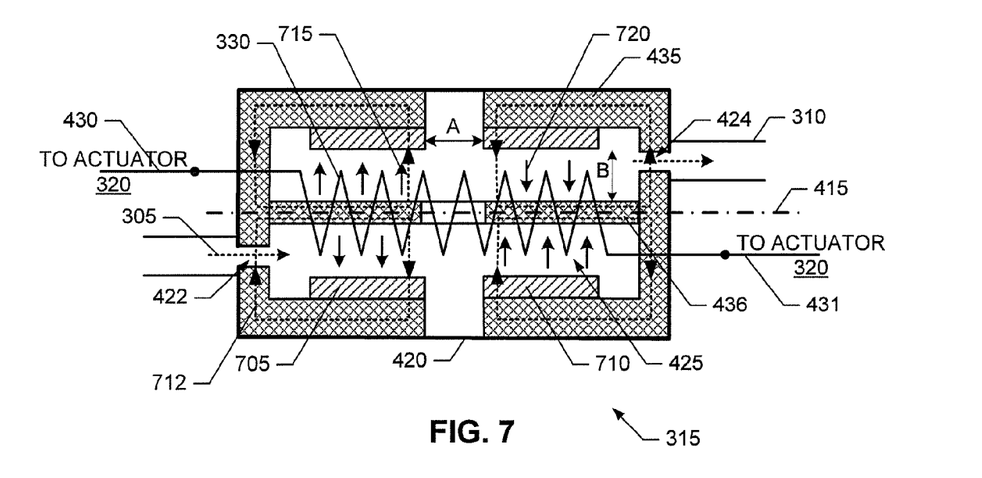

FIG. 7 is a side cross-sectional view of yet another example implementation of the vibrating helical spring sensor 315 of FIG. 3. The example helical spring 330 of FIG. 7 can be vibrated at its second overtone, that is, at twice its resonant frequency $f_p$. Because elements of the example vibrating helical spring sensor 315 of FIG. 7 are identical to those discussed above in connection with FIGS. 4 and 5, the description of identical elements is not repeated here. Instead, identical elements are illustrated with identical reference numerals in FIGS. 4, 5 and 7, and the interested reader is referred back to the descriptions presented above in connection with FIGS. 4 and 5 for a complete description of those like numbered elements.

In the illustrated example of FIG. 7, two cylindrical permanent magnets 705 and 710 are placed at opposite ends of the helical spring sensor 315. The example permanent magnets 705 and 710 of FIG. 7 have opposite polarities and, thus, generate respective radially symmetric magnetic fields 715 and 720 of opposite direction, as shown in FIG. 7. In the example of FIG. 7, the high relative magnetic permeable materials 435 and 436 have a gap corresponding to the gap between the magnets 705 and 710. To prevent magnetic flux leak, the distance A between the magnets 705 and 710 is greater than the distance B between the magnets 705 and 710 and the material 436. Because the example materials 435 and 436 are in contact with each other in the example of FIG. 7, they collectively form closed magnetic loops of magnetic flux, one of which is designated at reference numeral 712, within the vibrating spring sensor 315 around the portions of the helical coil 330 encompassed by the materials 435 and 436.

If a current 322 (FIG. 3) alternating at the resonant frequency $f_p$ of the helical coil 330 is passed through the example helical coil 330 of FIG. 7, the portions of the helical coil 330 surrounded by the example magnets 705 and 710 will vibrate at twice the resonant frequency $f_p$, with the middle portion of the helical coil 330 shrinking and expanding along the longitudinal axis 415.

Figure 11:
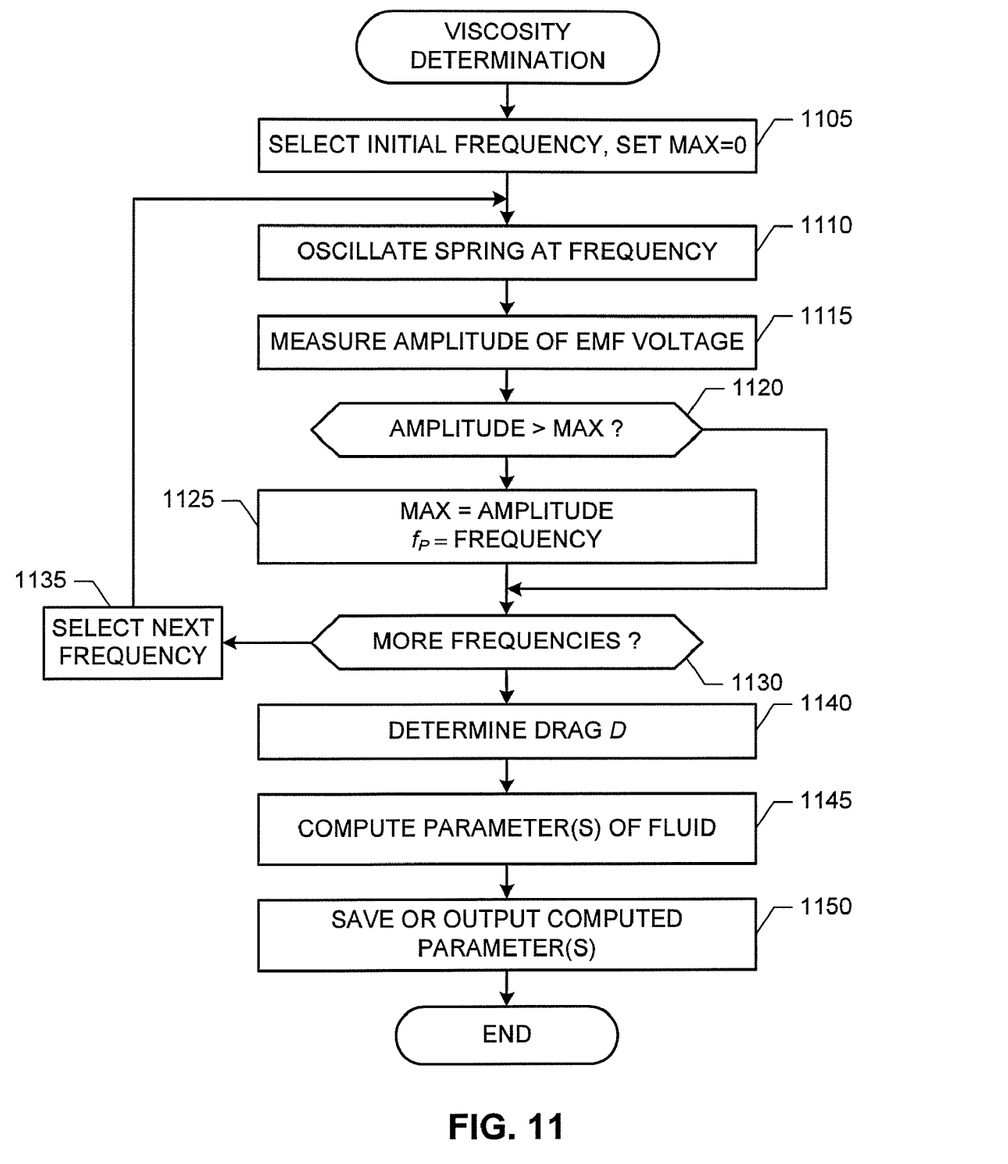
FIG. 11 illustrates an example process that may be carried out to perform fluid analysis using the example fluid analysis assemblies of FIGS. 1-7.

FIG. 11 is a flowchart representative of an example process that may be carried out to implement the example fluid analysis assemblies 26, 26a and 300 of FIGS. 1-3. The example process of FIG. 11 may be carried out by a processor, a controller and/or any other suitable processing device. For example, the example process of FIG. 11 may be embodied in coded instructions stored on an article of manufacture such as any tangible computer-readable and/or computer-accessible medium. Example tangible computer-readable medium include, but are not limited to, a flash memory, a compact disc (CD), a digital versatile disc (DVD), a floppy disk, a read-only memory (ROM), a random-access memory (RAM), a programmable ROM (PROM), an electronically-programmable ROM (EPROM), and/or an electronically-erasable PROM (EEPROM), an optical storage disk, an optical storage device, magnetic storage disk, a magnetic storage device, and/or any other tangible medium which can be used to store and/or carry program code and/or instructions in the form of machine-accessible and/or machine-readable instructions or data structures, and which can be accessed by a processor, a general-purpose or special-purpose computer, or other machine with a processor (e.g., the example processor platform P100 discussed below in connection with FIG. 12). Combinations of the above are also included within the scope of computer-readable media. Machine-readable instructions comprise, for example, instructions and/or data that cause a processor, a general-purpose computer, special-purpose computer, or a special-purpose processing machine to implement one or more particular processes. Alternatively, some or all of the example process of FIG. 11 may be implemented using any combination(s) of ASIC(s), PLD(s), FPLD(s), FPGA(s), discrete logic, hardware, firmware, etc. Also, some or all of the example process of FIG. 11 may instead be implemented manually or as any combination of any of the foregoing techniques, for example, any combination of firmware, software, discrete logic and/or hardware. Further, many other methods of implementing the example operations of FIG. 11 may be employed. For example, the order of execution of the blocks may be changed, and/or one or more of the blocks described may be changed, eliminated, sub-divided, or combined. Additionally, any or all of the example process of FIG. 11 may be carried out sequentially and/or carried out in parallel by, for example, separate processing threads, processors, devices, discrete logic, circuits, etc.

The example process of FIG. 11 begins with the example analysis module 345 of FIG. 3 selecting an initial frequency and setting a variable MAX=0 (block 1105). The example actuator 320 passes an alternating current 322 at the selected frequency through the helical spring 330 to oscillate the helical spring 330 (block 1110) and the induced voltage measurer 325 measures the emf voltage(s) 340 induced by the oscillation of the helical spring 330 (block 1115).

If the amplitude of the emf voltage 340 is greater than the variable MAX (block 1120), the variable MAX is set equal to the measured amplitude and a variable $f_p$ is set equal to the currently selected frequency (block 1125). If there are more frequencies to test (block 1130), a next frequency is selected (block 1135) and control returns to block 1110 to oscillate the helical spring 330 at the newly selected frequency.

If there are no more frequencies to test (block 1130), the analysis module 345 determines and/or computes the dragging force D using, for example, one of the example methods discussed above in connection with FIGS. 8-10 (block 1140). The analysis module 345 computes one or more parameters of the fluid 305, such as viscosity $\eta$ and/or density $\rho_f$, using, for example, one of the methods described above in connection with FIG. 3 (block 1145). The output interface 350 saves the computed parameter(s) in the storage 360 and/or transmits the computed parameters) to the surface via the telemetry module 355 (block 1150). Control then exits from the example process of FIG. 11.

Returning to block 1120, if the amplitude of the emf voltage 340 is not greater than the variable MAX (block 1120), control proceeds to block 1130 to determine whether there are more frequencies to test.

Figure 12:
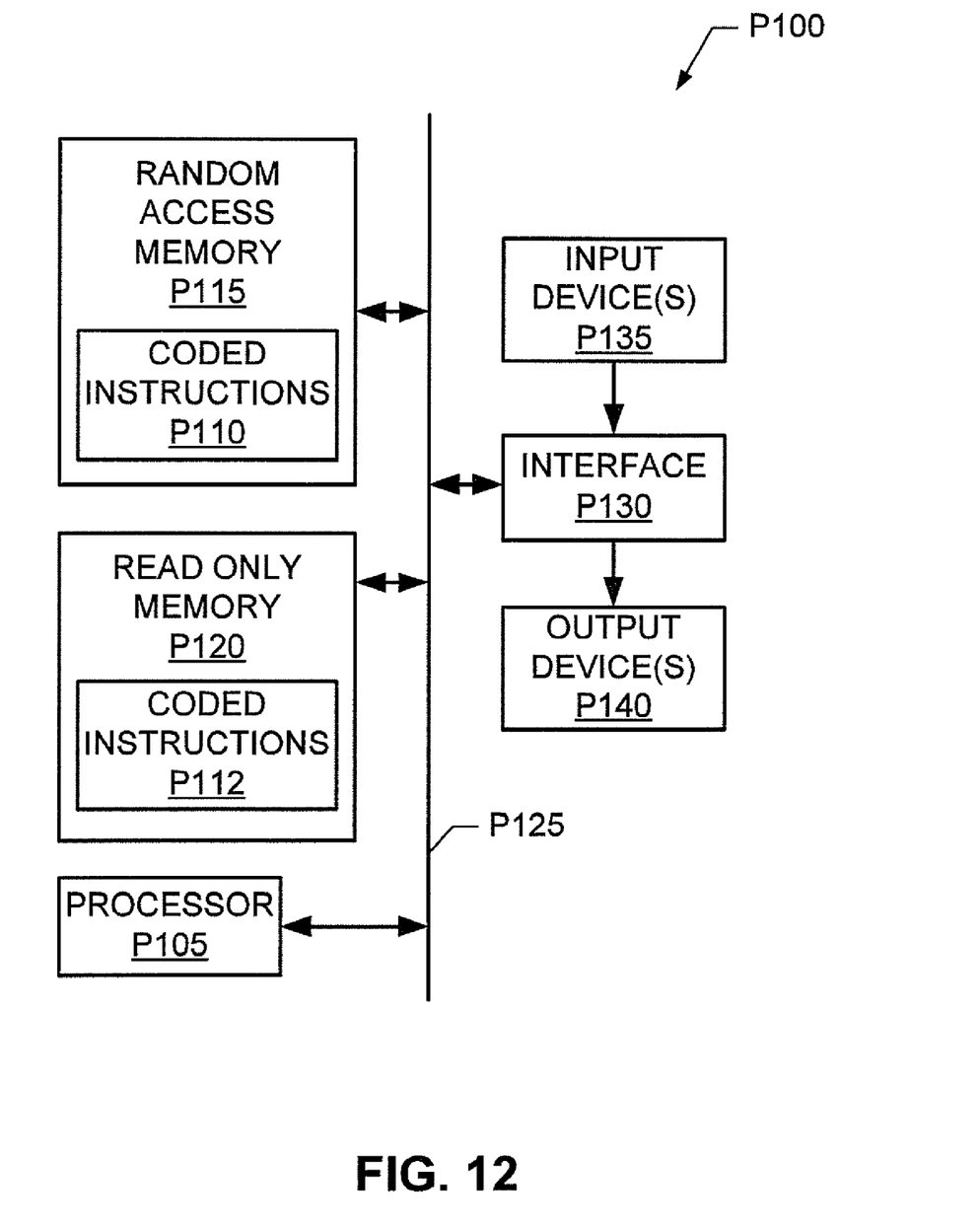
FIG. 12 is a schematic illustration of an example processor platform that may be used and/or programmed to carry out the example process of FIG. 11, and/or to implement any of all of the methods, apparatus and articles of manufacture disclosed herein.

FIG. 12 is a schematic diagram of an example processor platform P100 that may be used and/or programmed to implement the example fluid analysis assemblies 26, 26a, and 300 described herein. For example, the processor platform P100 can be implemented by one or more general-purpose processors, processor cores, microcontrollers, etc.

The processor platform P100 of the example of FIG. 12 includes at least one general-purpose programmable processor P105. The processor P105 executes coded instructions P110 and/or P112 present in main memory of the processor P105 (e.g., within a RAM P115 and/or a ROM P120). The processor P105 may be any type of processing unit, such as a processor core, a processor and/or a microcontroller. The processor P105 may execute, among other things, the example process of FIG. 11 to implement the example methods, apparatus and articles of manufacture described herein.

The processor P105 is in communication with the main memory (including a ROM P120 and/or the RAM P115) via a bus P125. The RAM P115 may be implemented by dynamic random-access memory (DRAM), synchronous dynamic random-access memory (SDRAM), and/or any other type of RAM device, and ROM may be implemented by flash memory and/or any other desired type of memory device. Access to the memory P115 and the memory P120 may be controlled by a memory controller (not shown). The memory P115, P120 may be used to implement the example storage 360.

The processor platform P100 also includes an interface circuit P130. The interface circuit P130 may be implemented by any type of interface standard, such as an external memory interface, serial port, general-purpose input/output, etc. One or more input devices P135 and one or more output devices P140 are connected to the interface circuit P130. The example output device P140 may be used to, for example, implement the example telemetry module 355.

Although certain example methods, apparatus and articles of manufacture have been described herein, the scope of coverage of this patent is not limited thereto. On the contrary, this patent covers all methods, apparatus and articles of manufacture fairly falling within the scope of the appended claims either literally or under the doctrine of equivalents.

What is claimed is:

1. An apparatus comprising:
   a housing;
   a helical spring held in tension;
   a flowline to expose the helical spring to a fluid;
   a magnet to expose the helical spring to a magnetic field, wherein the magnetic field radiates radially from an axis of the helical spring; and
   a wire to electrically conduct an actuating current through the helical spring to displace the helical spring.

2. An apparatus as defined in claim 1, wherein the helical spring comprises electrically conductive wire.

3. An apparatus as defined in claim 1, wherein the helical spring comprises at least one of Tungsten or a Tungsten alloy.

4. An apparatus as defined in claim 1, wherein the helical spring and the housing have a substantially similar thermal expansion coefficient.

5. An apparatus as defined in claim 1, wherein the helical spring is to vibrate in response to the actuating current and the magnetic field.

6. An apparatus as defined in claim 1, further comprising a sensor to detect an electromotive force (emf) voltage induced by displacement of the helical spring.

7. An apparatus as defined in claim 1, further comprising an analysis module to estimate a viscosity of the fluid based an electromotive force (emf) voltage induced across the helical spring.

8. An apparatus as defined in claim 1, further comprising an analysis module to estimate a density of the fluid based an electromotive force (emf) voltage induced across the helical spring.

9. An apparatus as defined in claim 1, wherein the actuating current comprises at least one of a transient signal, a steady-state signal, or an alternating current signal.

10. An apparatus as defined in claim 1, wherein the actuating current is to pass through only a portion of the helical spring.

11. An apparatus as defined in claim 1, wherein the magnetic field encompasses only a first portion of the helical spring.

12. An apparatus as defined in claim 11, wherein the magnetic field encompasses a second portion of the helical spring, the first portion separated from the second portion.

13. An apparatus as defined in claim 12, further comprising a second magnet having a first polarity and disposed about the first portion of the helical spring, wherein the magnet has a second polarity opposite the first polarity and is disposed about the second portion of the helical spring.

14. An apparatus as defined in claim 1, wherein the magnet comprises Samarian-cobalt (SmCo).

15. An apparatus as defined in claim 1, further comprising a magnetic circuit to prevent the housing or a second magnetic field from interfering with the magnetic field.

16. An apparatus as defined in claim 1, further comprising a high relative magnetic permeable material to form a magnetic circuit within the housing.

17. An apparatus as defined in claim 1, wherein the housing comprises a cylindrical shape.

18. A method comprising:
positioning a helical spring within a fluid;
exposing the helical spring to a magnetic field, wherein the magnetic field radiates radially from an axis of the helical spring;
passing a current through the helical spring to displace the helical spring within the fluid;
measuring an electromotive force (emf) voltage induced across the helical spring by the displacement; and
estimating a characterizing parameter of the fluid from the measured emf voltage.

19. A method as defined in claim 18, further comprising forming a magnetic field around at least a portion of the helical spring, wherein the displacement of the helical spring is responsive to the current and the magnetic field.

20. A method as defined in claim 18, wherein the current comprises at least one of a transient signal, a steady-state signal, or an alternating current.

21. A method as defined in claim 18, wherein the characterizing parameter of the fluid comprises at least one of a viscosity of the fluid or a density of the fluid.

22. A method as defined in claim 18, wherein the displacement of the helical spring comprises a resonant vibration.

23. An apparatus comprising:
a helical spring held under tension in a fluid passageway;
an actuating device to induce a displacement of the helical spring while a fluid is present in the fluid passageway, wherein the actuating device comprises a magnet to expose the helical spring to a magnetic field, the magnetic field radiating radially from an axis of the helical spring, and a wire to electrically conduct an actuating current through the helical spring; and
an interpretation module to estimate a parameter of the fluid based the induced displacement of the helical spring.

24. An apparatus as defined in claim 23, wherein the interpretation module is to estimate a drag force based on the induced displacement, to define a fluid analysis model based on the estimated drag force, and to solve the fluid analysis model for the parameter of the fluid.

25. An apparatus as defined in claim 23, wherein the parameter of the fluid comprises at least one of a viscosity of the fluid or a density of the fluid.

* * * * *